(12) United States Patent
Nakagawa (10) Patent No.: US 11,607,562 B2
(45) Date of Patent: Mar. 21, 2023

(54) SYSTEM OF AND METHOD FOR PARTICLE BEAM RADIOTHERAPY

(71) Applicant: Keiichi Nakagawa, Tokyo (JP)

(72) Inventor: Keiichi Nakagawa, Tokyo (JP)

( * ) Notice: Subject to any disclaimer, the term of this patent is extended or adjusted under 35 U.S.C. 154(b) by 0 days.

(21) Appl. No.: 17/187,740

(22) Filed: Feb. 27, 2021

(65) Prior Publication Data

US 2021/0370095 A1    Dec. 2, 2021

(51) Int. Cl.
*A61N 5/10* (2006.01)

(52) U.S. Cl.
CPC .......... *A61N 5/1045* (2013.01); *A61N 5/1077* (2013.01); *A61N 2005/1089* (2013.01)

(58) Field of Classification Search
None
See application file for complete search history.

(56) References Cited

U.S. PATENT DOCUMENTS

| | | | |
|---|---|---|---|
| 10,485,993 B2* | 11/2019 | Goer | A61N 5/1049 |
| 2018/0015304 A1* | 1/2018 | Oh | A61N 5/1049 |
| 2021/0187325 A1* | 6/2021 | Liu | A61N 5/1065 |

* cited by examiner

*Primary Examiner* — Hoon K Song (57) ABSTRACT

A particle beam radiotherapy system has been proposed by using a set of first and second scatterers, whereby a short-duration pulse beam is irradiated to a lesion. When the duration of the radiotherapy beam is 200 milliseconds or less, healthy tissues are selectively protected and only cancer tissues are damaged. For example, it can be used for cancer treatment of brain metastases that may be distributed throughout the entire brain tissues. The positions of the scatterers and the energy of the incident particle beams are optimized according to the position and the volume of the brain tissues.

14 Claims, 7 Drawing Sheets

SYSTEM OF AND METHOD FOR PARTICLE BEAM RADIOTHERAPY

TECHNICAL FIELD

The present invention relates generally to a system of and a method for particle beam radiotherapy, and more particularly, to an improved system of and an improved method for particle beam radiotherapy that can cure cancers whilst minimizing normal tissue complications.

BACKGROUND ART

A particle beam radiotherapy unit is described in detail in a Japanese patent granted as JP3751440B2, and an entire English translation is available in https://patents.google.com/patent/JP3751440B2/en?oq=JP3751440B2, the disclosure of which is hereby incorporated by reference.

Figure 1:
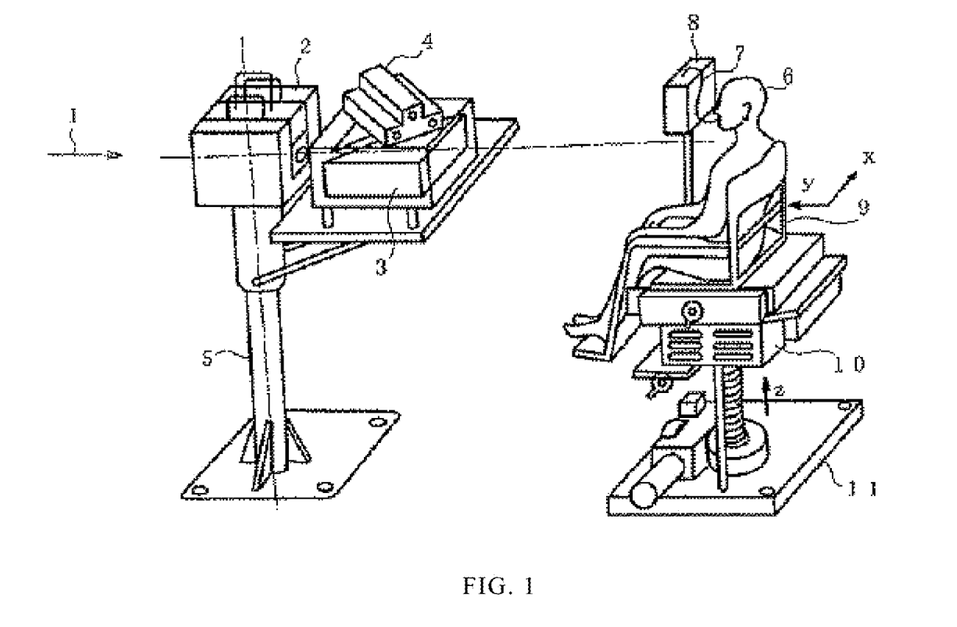
FIG. 1 is a perspective view of conventional proton therapy equipment.

FIG. 1 shows a perspective view of a particle beam radiotherapy system disclosed in a research article published in 1994 by Abazov et al. as a JINR publication, E-18-94-112. Medical facility for radiation therapy with JINR proton phasotron beams, and its PDF document is available in http://cds.cern.ch/record/266612?ln=ja, the disclosure of which is hereby incorporated by reference. FIG. 1 also appears in the above Japanese patent as a prior art.

In this figure, the numeral 1 indicates a proton beam irradiated from an accelerator (not shown), the numeral 2 depicts a collimator for producing a narrow beam necessary for irradiation only to a small tumor, and the numeral 3 is an energy degrader (attenuator) that allows the beam to stop at a predetermined body depth where a tumor is located. The numeral 4 is a manipulator for controlling the gap width of the energy degrader 3 by a computer (not shown), and the numeral 5 is a stand on which the collimator 2, the energy degrader 3 and the manipulator 4 are installed.

Reference numeral 6 denotes a patient to be treated. In this example, an esophageal cancer is treated with a proton beam. A radiation dose detector (not shown) that detects the dose delivered by the proton beam is inserted into the patient's esophagus through a tube 7. The numeral 8 is a monitor for monitoring the output of the detector, and 9 is a treatment chair on which the patient 6 sits. The numeral 10 denotes a drive mechanism that rotates and translates the treatment chair 9 in the vertical and horizontal directions, and 11 denotes a stand of the treatment chair 9 and the drive mechanism 10.

Next, the operation is described. After the detector is inserted into the esophagus via the tube 7, the patient 6 is translated in the vertical and horizontal directions by the drive mechanism 10, so that an esophageal tumor is accurately located on a path of the proton beam 1. When the adjustment of the position of the patient 6 is completed, the proton beam 1 is irradiated from the accelerator, the cross section of the beam 1 is reduced by the collimator 2. The energy of the beam 1 is attenuated by the energy degrader 3, and the tumor inside the patient 6 is irradiated. In actual treatment, the beam 1 is delivered while the treatment chair 9 is rotated on a horizontal plane. During the beam delivery, the energy of the beam 1 is continuously adjusted by the energy degrader 3 so that a maximum dose is always absorbed by the esophageal tumor while the patient 6 is rotated.

Figure 2:
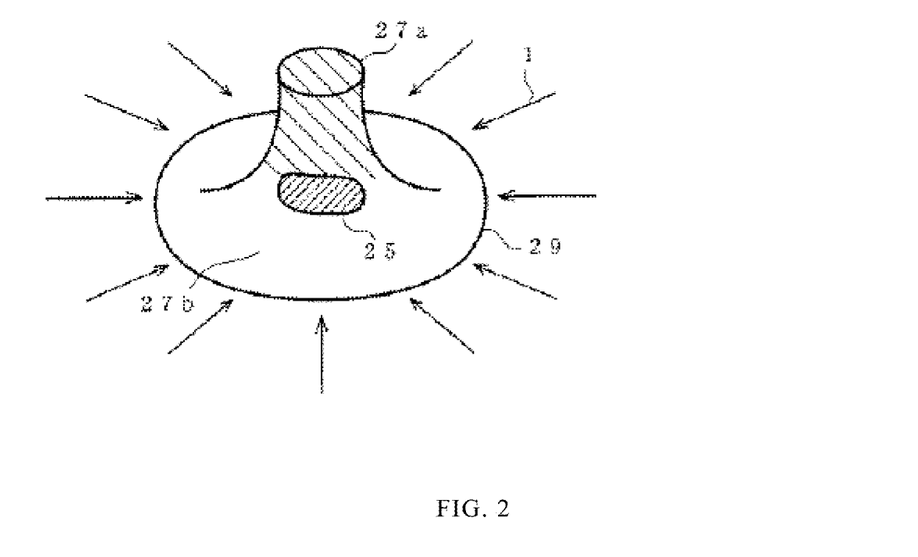
FIG. 2 shows a dose distribution generated inside the patient body when a tumor is positioned at the rotation center of the device in FIG. 1 and the proton beam is delivered while rotating the patient.

FIG. 2 shows a dose distribution generated in the body when the tumor 25 is positioned at the rotation center and irradiated with a proton beam 1 while rotating the patient 6. The numeral 27a shows a high dose region inside the tumor 25, whereas 27b indicates a low dose region in normal tissues surrounding the tumor 25 in the patient body 29.

When the tumor is large, the beam size needs to be enlarged to cover the entire tumor volume. A method for expanding the irradiation field is described in "Tommasino F et al. A new facility for proton radiobiology at the Trento proton therapy centre: design and implementation. Phys Med. 2019; 58:99-106", the disclosure of which is hereby incorporated by reference.

Figure 3:
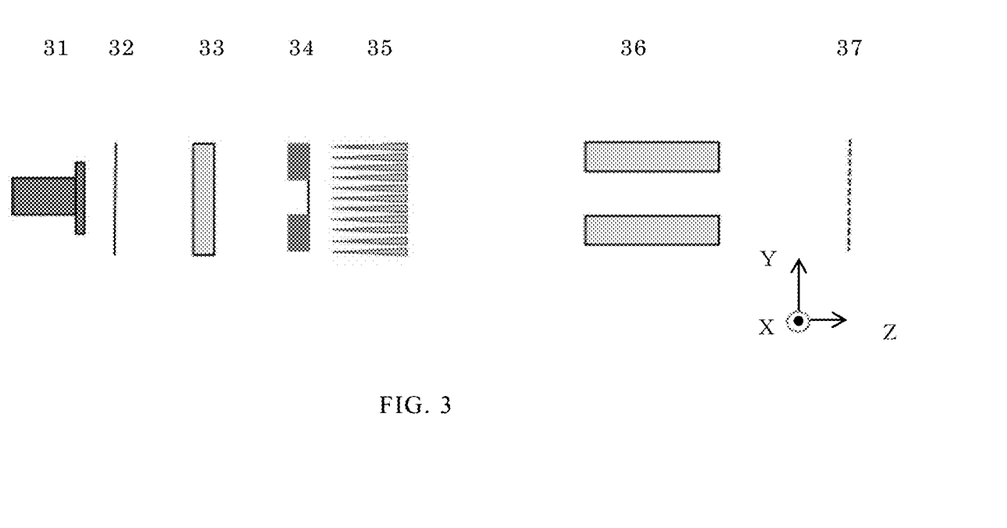
FIG. 3 is a diagram of a conventional proton beam irradiation device.

FIG. 3 is a diagram of a proton beam irradiation apparatus shown in this publication, wherein 31 is a beam entrance pipe placed at a beam injection point and 32 is a thin metal foil, and the irradiation field size of the beam is expanded. 33 is a monitor dosimeter, 34 is a second scatterer having a double ring structure, 35 is a depth dose modulator that adjusts the dose distribution in the depth direction to cover the entire length of the target, 36 is a collimator for adjusting the cross section of radiation field according to the target shape, and 37 is a plane where the target is positioned.

Figure 4:
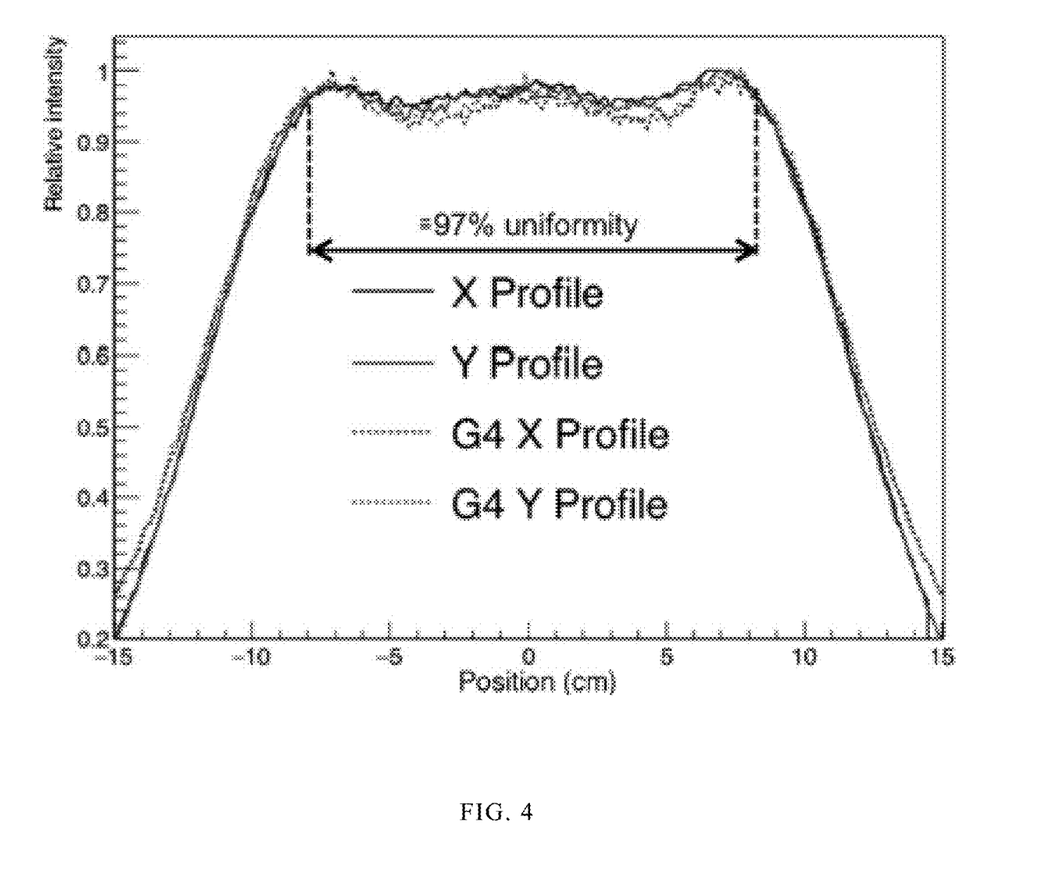
FIG. 4 shows a dose distribution, generated by the apparatus in FIG. 3, in a direction perpendicular to the incident beam direction.

The solid line of FIG. 4 shows a measured dose distribution in a plane perpendicular to the irradiation direction generated by the apparatus of FIG. 3, and shows that a nearly uniform dose can be given by the first scatterer 32 and the second scatterer 34. Hereinafter, the dose distribution in the plane perpendicular to the irradiation direction is called a lateral dose distribution.

In FIG. 4, X and Y show the coordinate axes on the plane perpendicular to the irradiation direction, as was also shown on the right-hand side in FIG. 3. The dotted lines labelled as G4 are calculated results using a Monte Carlo code, GEANT4, which was used for double-checking purpose.

Figure 5:
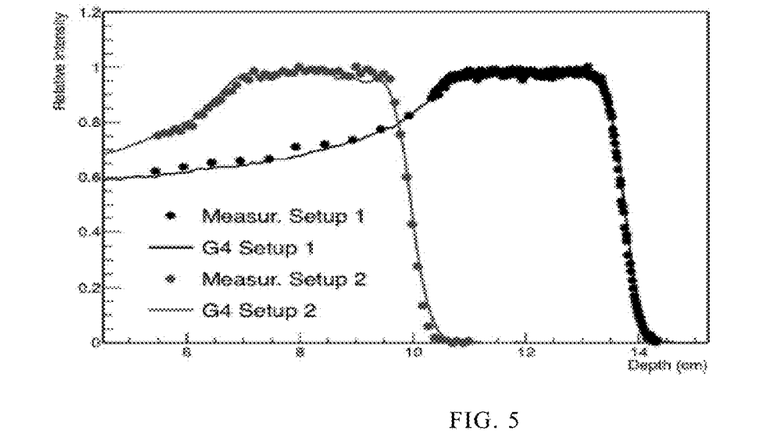
FIG. 5 is a dose distribution, generated by the apparatus in FIG. 3, in the depth direction.

FIG. 5 shows dose distributions in the depth direction generated by the apparatus of FIG. 3, showing that the depth dose modulator 35 can produce a uniform high dose distribution that can match the length of the tumor. The filled circles in FIG. 5 show measured values, whereas the lines labelled as G4 show the results of Monte Carlo calculation using the GEANT4. FIG. 5 also shows that by changing the incident proton beam energy, the depth of a uniform high dose distribution can be adjusted.

In the meantime, when many metastatic brain tumors are detected by CT or MRI, a standard X-ray radiotherapy may be whole brain radiotherapy that delivers a daily dose of 2 grays to the entire brain, which is repeated for 15 days, for example. This is because there are presumably many metastatic tumors that are too small to be detected. On the other hand, it is known that the whole brain radiotherapy may induce cognitive damage to the normal brain. A better radiotherapy technique is therefore needed.

In conventional particle therapy equipment, a fraction dose of 2 grays is prescribed to the tumor, for example, and the total dose is about 60 grays, for example, in order to protect normal tissue adjacent to the tumor. It is known that higher total dose to the tumor results in higher local control rate of the tumor; however, the dose to the adjacent normal tissues also increases at the same time, leading to higher complication probability.

Recently, a new radiation therapy has been highlighted in which the irradiation duration is set to 200 milliseconds or less, more preferably 100 milliseconds or less, thereby suppressing normal tissue complication. For example, when the brain of a mouse is irradiated with a large dose of 10 grays at a time, cognitive impairment hardly occurred if the dose rate was raised to 100 grays per second or more, and thus the irradiation duration was 100 milliseconds or less. This results were described in "Montay-Gruel P et al. Irradiation in a flash: Unique sparing of memory in mice after whole brain irradiation with dose rates above 100 Gy/s. Radiother Oncol. 2017; 124:365-369", the disclosure of which is hereby incorporated by reference.

As was already mentioned, when there are many early stage metastatic brain tumors that are difficult to detect by CT or MRI, whole brain irradiation is often employed. The above reference reported by Montay-Gruel P shows that normal brain tissues can be protected if a large dose is irradiated to the entire brain with an irradiation duration less than or equal to 100 milliseconds.

The dose rate of the clinically available X-ray therapy apparatus can generate a dose rate of about 5 grays to 20 grays per minute, and an irradiation duration of 30 seconds to several minutes or more is required in order to give a dose of about 10 grays. Proton beams are another radiotherapy beams other than X-rays. The dose rate of the clinical proton beam apparatus is about 5 grays per minute at most, a typical irradiation duration is expected to be about a few minutes or more, and it is impossible to set the irradiation duration down to 100 milliseconds to 200 milliseconds or less.

Recently, a report was published that can increase the dose rate of proton therapy equipment using a cyclotron-based design, leading to a dose rate of about 100 grays per second, which is described in "Diffenderfer E S et al. Design, implementation, and in vivo validation of a novel proton FLASH radiation therapy system. Int J Radiat Oncol Biol Phys. 2020; 106:440-448", the disclosure of which is hereby incorporated by reference. Nevertheless, it was not possible to irradiate the entire human brain in less than 100 milliseconds because the proton beams needed to be scanned within the entire brain volume from several different irradiation directions, which required much longer period of time.

SUMMARY

In order to solve the above mentioned problems, the present invention relates to a system of and a method for a particle beam radiotherapy, in which particle beams such as proton beams or carbon beams are irradiated from a single irradiation direction with an irradiation duration of about 200 milliseconds or less, more preferably 100 milliseconds or less. The first and second scatterers described in FIG. 3, for example, are employed to obtain a larger size of the irradiation field as shown in FIG. 4 that can cover the entire brain. By placing the entire brain inside a nearly flat dose region in the depth direction, whole brain irradiation can be realized within 100 milliseconds or less. A dose prescription of 10 grays is considered reasonable for whole brain irradiation, because little cognitive impairment of the brain occurred in the aforementioned publication reported by Montay-Gruel P.

In accordance with one embodiment, a system of particle beam radiotherapy comprises an accelerator that generates therapeutic particle beams; a transport means for transporting the particle beams generated by the accelerator; a beam size expansion means for enlarging the beam size; a collimation means for matching a cross section of the particle beams with a cross section of an object of irradiation; a control means for controlling the accelerator, the beam size expansion means and the collimation means, whereby the control means restricts the irradiation duration of the particle beams to be less than or equal to 200 milliseconds; a beam stop means for stopping the particle beam after the particle beam passes through the object of irradiation; a positioning means for positioning the object of irradiation; an energy determination means for determining the energy of the particle beams in such a way that a volume of the object of irradiation is positioned inside a region of nearly flat dose deposition on a proximal side of a Bragg peak generated by the particle beams.

In accordance with another embodiment, a method for particle beam radiotherapy comprises positioning an object of irradiation by using a positioning means, positioning a set of first and second scatterers by using a control means, determining an energy of particle beams in such a way that a volume of the object of irradiation is positioned inside a region of nearly flat dose deposition on a proximal side of a Bragg peak generated by the particle beams, activating a collimation means in order to match a cross section of the particle beams with a cross section of the object of irradiation, and delivering the particle beams for a period of 200 milliseconds or less.

Advantages

According to the present invention, the irradiation period of the particle beam can be shortened down to at least 200 milliseconds or less; and therefore, the complication of healthy tissues can be much reduced while maintaining a high control capability of the cancer. Furthermore, since a larger dose can be safely delivered without damaging the healthy tissues, the irradiation can be, for example, just one time, thereby resulting in a very efficient treatment.

REFERENCE NUMERALS IN THE DRAWINGS

1 Proton beam
2 Collimator
3 Energy degrader
4 Manipulator
5 Stand
6 Patient
7 Tube
8 Monitor
9 Treatment chair
10 Drive mechanism
11 Stand
25 Tumor
27a High dose region inside the tumor
27b Low dose region in normal tissues
29 Patient's body
31 Beam entrance pipe
32 First scatterer
33 Monitor dosimeter
34 Second scatterer
35 depth dose modulator
36 Collimator
37 Target location
41 Accelerator
42 Transport means
43 First scatterer
44 Second scatterer
44a Hollow cylinder
44b Cylinder
45 Collimator
45a Leaf of the collimator
45b Leaf of the collimator
47 Control means
48 Beam stop means
49 Patient
50 Treatment chair
51 Parietal positioning means
52 Rods
53 Chin positioning means
58 Treatment couch Suitable embodiments of a system of and a method for particle beam radiotherapy according to the present invention will be described in the following details with reference to the attached drawings.

Detailed Description: First Embodiment with FIGS. 6-13

Figure 6:
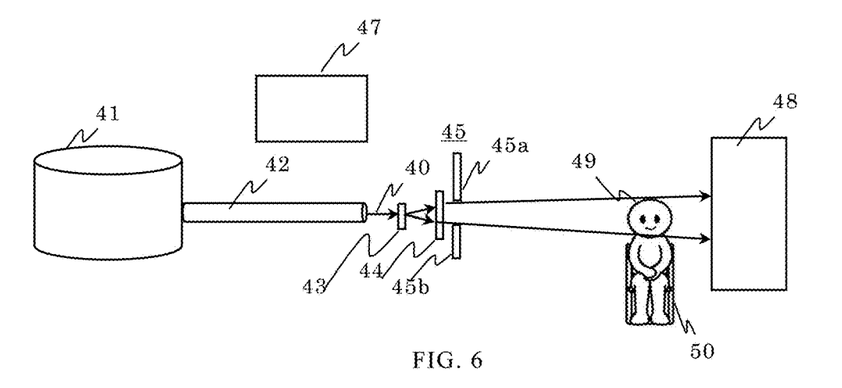
FIG. 6 is a diagram showing a proton radiotherapy system according to the present embodiment

FIG. 6 is a diagram of a particle beam radiotherapy system according to the present invention comprising a cyclotron type accelerator 41 that generates a therapeutic proton beam; a transport means 42, such as a beam transport tube, that propagates the proton beam toward a treatment area; a set of a first scatterer 43 and a second scatterer 44 that expands the field size of the proton beam; a collimator 45 that matches the field shape of the proton beam with a shape of a irradiation object (in this case, a whole brain of a patient 49); a control means 47, such as a computer, for controlling the accelerator 41, a set of the first scatterer 43 and the second scatterer 44, and the collimator 45 by connecting control signal cables in between. For readability of FIG. 6, these cables are not shown. The incident beam passes through a side of the head of the patient 49, and then reached a beam stop means 48 where the proton beam stops. 50 is a treatment chair for the patient 49.

Figure 7:
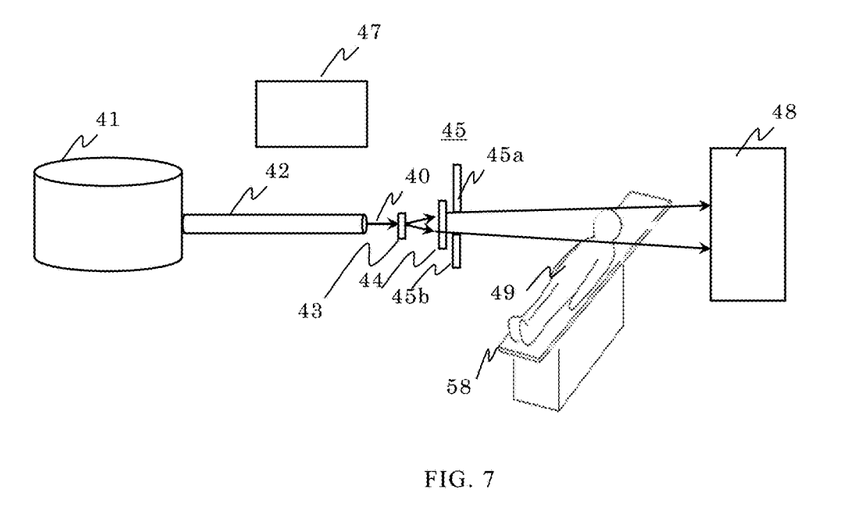
FIG. 7 is a diagram showing another proton radiotherapy system according to this embodiment.

FIG. 7 is a slightly different diagram where the patient 49 is placed on a treatment couch 58 and the beam passes through the side of the head and reaches the beam stop means 48. Others are the same as those described in FIG. 6.

In FIG. 6, when the first scatterer 43 and the second scatterer 44 are positioned at optimal positions by the control means 47 in reference to the position of the patient 49 seated on the treatment chair 50, a monoenergetic proton beam 40 can provide a nearly uniform dose distribution in the lateral direction as illustrated in FIG. 4. Here, the irradiation target is the entire brain and therefore the treatment is called whole brain irradiation. To protect surrounding body portions such as the neck and the chest, the opening of the collimator 45, such as a multileaf collimator, needs to be optimally placed, which is, for instance, achieved by moving leaves 45a and 45b of the collimator 45 to optimum positions using the control means 47 before irradiation.

In FIGS. 6 and 7, proton beams passing through the patient's head stop at the beam stop means 48 installed behind. The beam stop means is, for example, an acrylic water tank or a polyethylene block having a sufficient size. If the water tank or the polyethylene block is configured to have a thickness sufficiently larger than the residual range of the proton beam, the proton beam stops inside the acrylic water tank or the polyethylene block for the purpose of radiation protection.

Figure 8:
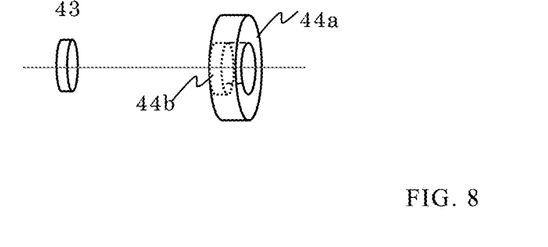
FIG. 8 is a diagram showing a set of the first and the second scatterers according to this embodiment.

FIG. 8 is a diagram of the first and the second scatterers. The first scatterer 43 is cylindrical, while the second scatterer 44 has a double ring structure composed of a hollow cylinder 44a and an inner cylinder 44b. For example, the first scatterer 43 is made of a lead or tungsten alloy having a thickness of several millimeters, the hollow cylinder 44a of the second scatterer is a light metal such as aluminum having a thickness of about 10 to 20 millimeters, and the cylinder 44b of the second scatterer uses a lead or tungsten alloy having a thickness of several millimeters. This is an example, and the material, thickness, and installation position can be selected with some degrees of freedom as long as the lateral dose distribution is approximately uniform within the irradiation object. Specific design examples are described in an aforementioned report published by Tommasino F.

Figure 9:
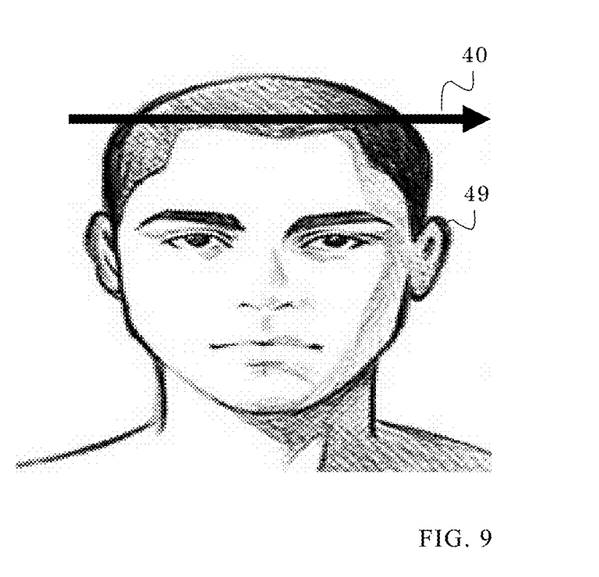
FIG. 9 is a depth dose distribution for various incident energies of proton beams according to this embodiment.

FIG. 9 shows depth dose distributions when incident monoenergetic proton beams having energies of 100, 150, 200 and 250 MeV (million electron volts) are delivered to a patient body. In each plot, the peak of the dose is called a Bragg peak. If the brain to be irradiated is positioned in the nearly flat dose region on a proximal side of the Bragg peak, a nearly uniform dose can be delivered to the entire brain. For example, in the case of whole brain irradiation, the beam 40 preferably passes through the side of the head of the patient 49 as shown at the bottom half of FIG. 9, and the typical head width (a horizontal length from the left end to the right end of the head) of the patient 49 is about 20 to 25 cm. Consequently, the irradiation depth in the direction of the beam transport is also about 20 to 25 cm. Referring to the depth dose plots shown at the upper half of FIG. 9, it is preferable to adjust the energy of the incident proton beam to about 250 MeV to 350 MeV.

Figure 10:
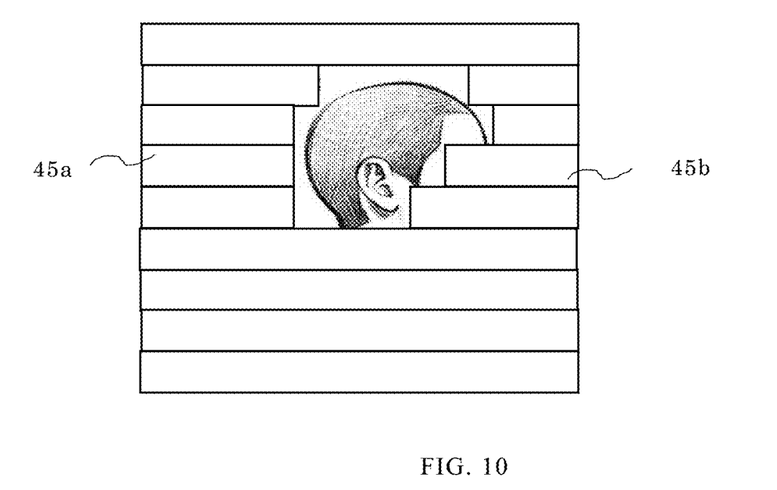
FIG. 10 is a diagram showing an example of collimator setting according to the present embodiment.
Figure 11:
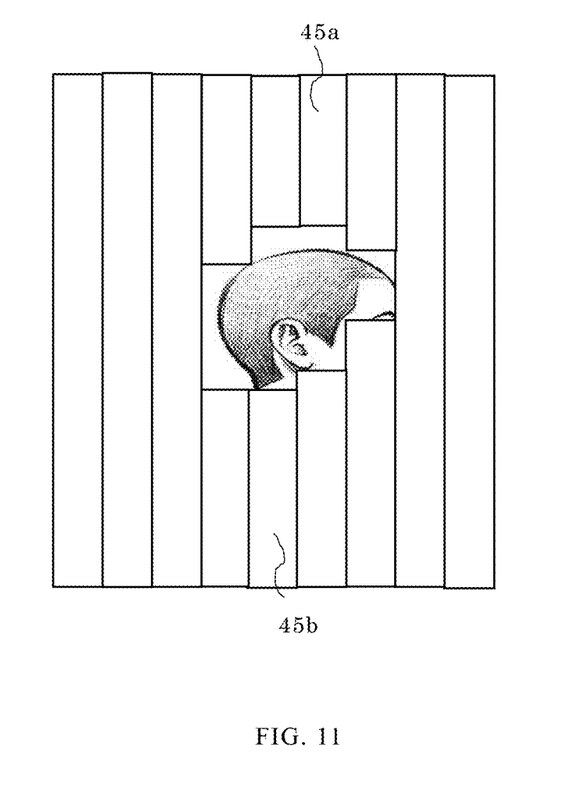
FIG. 11 is another diagram showing another example of collimator setting according to the present embodiment.
Figure 12:
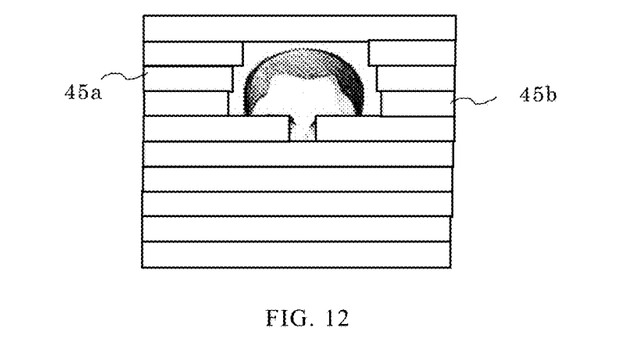
FIG. 12 is a diagram showing still another example of collimator setting according to the present embodiment

FIGS. 10, 11, and 12 are examples of placement of leaves 45a and 45b of the collimator 45. FIGS. 10 and 11 are cases when the beam is irradiated from the side of the head, and FIG. 12 is a case in which the patient is placed on a chair and the beam is irradiated from the front of the head. A known multileaf collimator having a large number of leaves is employed as a collimator 45 in these figures, and positions of leaves 45a and 45b are adjusted to protect healthy tissues surrounding the brain target by the control means 47.

Considering the actual three-dimensional structure of the brain, FIG. 10 or 11 are preferable due to better protection of healthy tissues. Each leaf of the multileaf collimator is driven by a motor which is not shown. The difference between FIGS. 10 and 11 is the direction of movement of the leaf. When the patient 49 is placed on the couch 58 as shown in FIG. 7, it is desirable to irradiate from the side of the head, and the movement direction of the multileaf collimator can be either horizontal or vertical as shown in FIG. 10 or 11.

Figure 13:
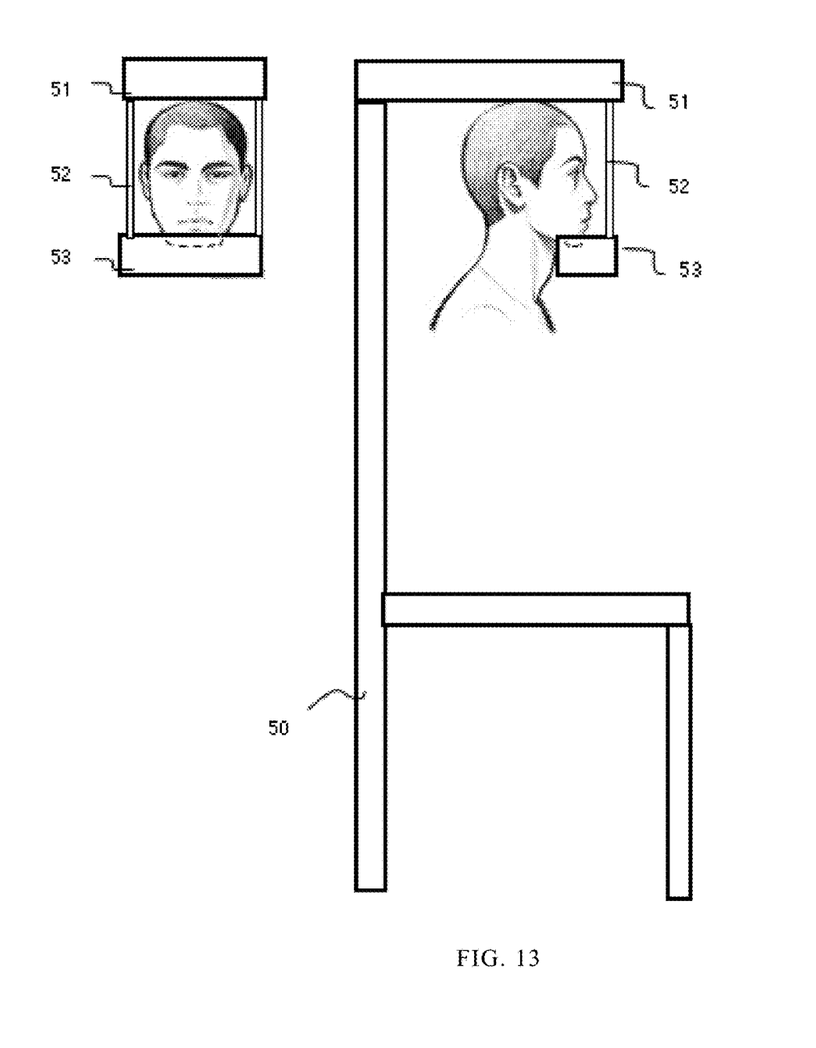
FIG. 13 is a diagram showing an example of a positioning means for positioning a head according to the present embodiment.

FIG. 13 shows a positioning means of the head when the patient is placed on a treatment chair 50. The numeral 53 indicates a chin positioning means made of thermoplastic resin that secures the chin. The shape of the chin positioning means is made by pressing it against the chin after warming up the resin by hot water. After cooling down, the resin becomes a solid positioning means. The numeral 51 is a parietal positioning means and is composed of materials such as acrylic resin. 52 is a plurality of rods for joining 51 and 53, and the distances of 51 and 53 are adjusted according to the size of the head. The parietal positioning means 51 is connected to the chair 50 where the patient sits. When the patient 49 is placed on the treatment couch 58 as shown in FIG. 7, the fixation of the head can be done by a known radiotherapy mask made of thermoplastic resin, which covers the entire head.

Detailed Description: Second Embodiment with FIG. 14

Figure 14:
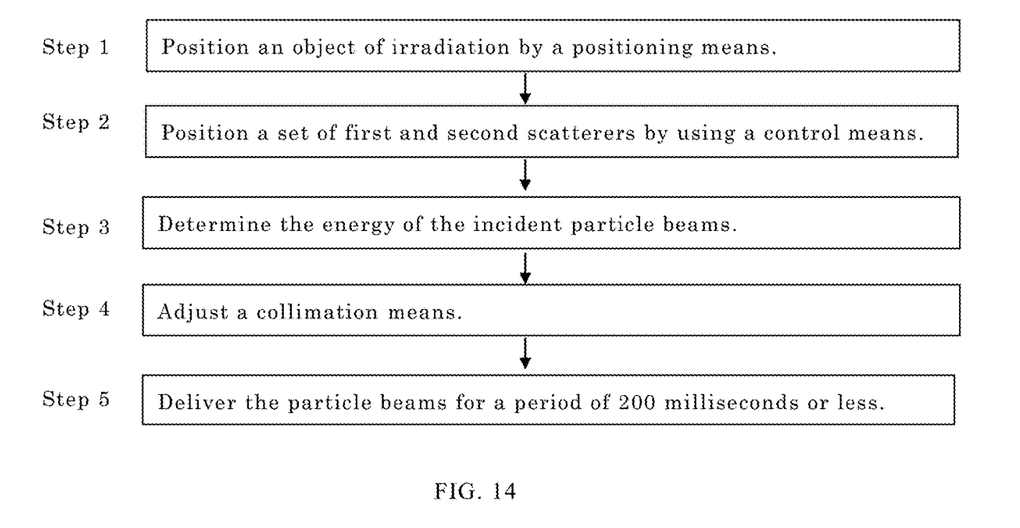
FIG. 14 is a flowchart showing an operation of the present particle radiotherapy.

FIG. 14 is a flowchart showing an embodiment of a method for a particle beam radiotherapy. In Step 1, the irradiation object, such as a human brain, is secured using a positioning means. In Step 2, the first and the second scatterers are positioned by a control means. In Step 3, the incident particle beam energy is determined. In Step 4, the opening of the collimator is adjusted. In Step5, the particle beam is irradiated for a predetermined period of about 200 milliseconds or less, more preferably 100 milliseconds or less. A method for positioning the human brain object has already been described in a previous embodiment by referring to FIG. 13.

Positioning the first and second scatterers in the Step 2 is performed by using the control means 47 of FIG. 6. By changing the position of the scatterers, the region giving a nearly uniform dose distribution in the lateral direction changes, so that the optimal positions may be selected according to the dimensions of the irradiation target, in this case the human brain.

The energy of the incident particle beams in the Step 3 may be about 250 MeV to 350 MeV when proton beams are employed, as was already described. However, the energy depends on the size of the irradiation object in the depth direction, and it is also possible to select the energy in a range of 200 MeV to 500 MeV. On the other hand, whole brain irradiation to children allows lower energy less than 200 MeV to be used.

In Step 4, the opening of the collimator, preferably a multileaf collimator having a plurality of leaves, is determined according to the target shape, so that only the target receives treatment dose whereas normal tissues surrounding the target are protected by the collimator leaves. The movement of the leaves are driven by motors which are controlled by the control means.

In Step 5, the particle beams are delivered for a predetermined period of about 200 milliseconds or less, more preferably 100 milliseconds or less, which is controlled by the control means 47 after pressing the irradiation start button provided in the control means 47.

Figure 15:
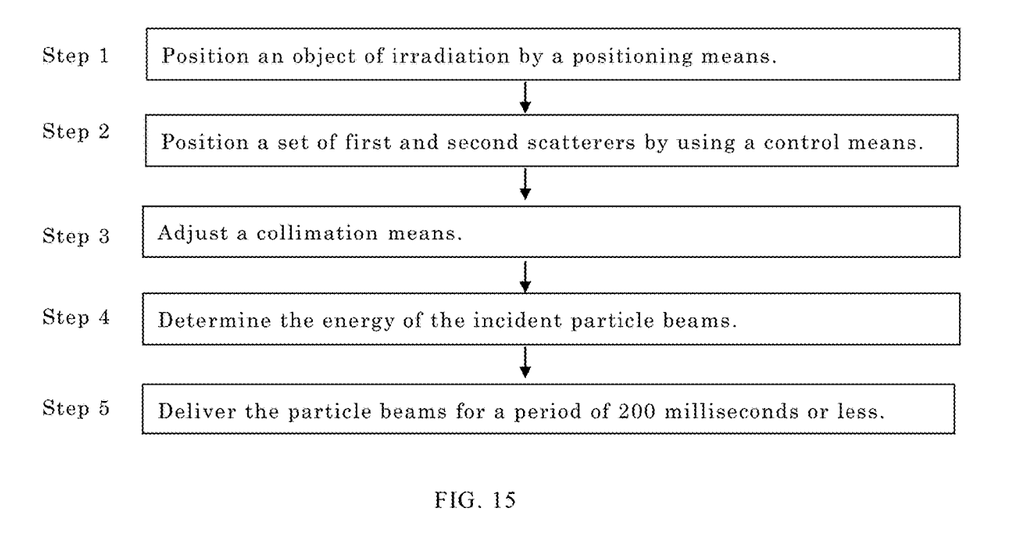
FIG. 15 is a slightly different flowchart showing another operation of the present particle radiotherapy, where the order of the step 3 and the step 4 in FIG. 15 is reversed against that in FIG. 14.

The execution order of Step 2, Step 3 and Step 4 may be arbitrarily swapped because those three actions are mutually independent. For example, FIG. 15 is a slightly different flowchart showing another example of how the present particle radiotherapy system is operated, where the order of the step 3 and the step 4 in FIG. 15 is reversed against that in FIG. 14.

The present invention is not limited to the above-described embodiments, and of course various configurations can be obtained without deviating from the gist of the present invention. For example, as the particle beams, not only proton beams but also other heavy ion particle beams such as carbon beams can be used. Further, if the irradiation field size is further expanded in FIG. 7, a larger tumor in the body or even whole body of the patient can be treated on the treatment couch by this invention.

Lastly, the scope of the embodiments should be determined by the appended claims and their legal equivalents, rather than by the examples given.

What is claimed is:
1. A system of particle beam radiotherapy, comprising: an accelerator that generates therapeutic particle beams; a transport means for transporting said particle beams generated by said accelerator; a beam size expansion means for enlarging said beam size; a collimation means for matching a cross section of said particle beams with a cross section of an object of irradiation; a control means for controlling said accelerator, said beam size expansion means and said collimation means, whereby said control means restricts an irradiation duration of said beams to be less than or equal to 200 milliseconds; a beam stop means for stopping said particle beam after said particle beam passes through said object of irradiation; a positioning means for positioning said object of irradiation; an energy determination means for determining the energy of said particle beams in such a way that a volume of said object of irradiation is positioned inside a region of nearly flat dose deposition on a proximal side of a Bragg peak generated by said particle beams.

2. The system of claim 1, wherein proton beams are employed as said particle beams.

3. The system of claim 1, wherein carbon beams are employed as said particle beams.

4. The system of claim 1, wherein a cyclotron is employed as said accelerator.

5. The system of claim 1, wherein a multileaf collimator is employed as a collimation means.

6. The system of claim 1, wherein a set of first and second scatterers is employed as a beam size expansion means.

7. The system of claim 2, wherein an energy of proton beams is selected in a range between 200 megaelectron volt and 500 megaelectron volt according to a volume and a position of said object of irradiation.

8. The system of claim 1, wherein said irradiation duration of 100 milliseconds or less is employed.

9. The system of claim 1, wherein said object of irradiation is a human brain.

10. The system of claim 1, wherein said object of irradiation is a human body.

11. A method for particle beam radiotherapy, comprising:
(a) positioning an object of irradiation by using a positioning means,
(b) positioning a set of first and second scatterers by using a control means,
(c) determining an energy of particle beams in such a way that a volume of said object of irradiation is positioned inside a region of nearly flat dose deposition on a proximal side of a Bragg peak generated by said particle beams,
(d) activating a collimation means in order to match a cross section of said particle beams with a cross section of said object of irradiation,
(e) delivering said particle beams for a period of 200 milliseconds or less.

12. The method of claim 11, wherein said object of irradiation is a human brain, and said positioning of said brain is performed by adjusting a distance between a chin positioning means and a parietal positioning means that are mutually connected by a plurality of rods.

13. The method of claim 11, wherein activating a collimation means is performed by moving a plurality of leaves of a multileaf collimator.

14. The method of claim 11, wherein said particle beams are delivered for a period of 100 milliseconds or less.

* * * * *